(12) United States Patent
Cherif-Cheikh et al.

(10) Patent No.: US 9,724,397 B2
(45) Date of Patent: Aug. 8, 2017

(54) SUSTAINED RELEASE FORMULATIONS COMPRISING VERY LOW MOLECULAR WEIGHT POLYMERS

(75) Inventors: Roland Cherif-Cheikh, Castelldefels (ES); Anne-Paula De Sousa Delgado, Moilins de Rei (ES); Frédéric Lacombe, Sant Cugat de Valles (ES); Laurence Lachamp, Gava (ES); Didier Bourissou, Plaisance du Touch (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 1037 days.

(21) Appl. No.: 12/447,431

(22) PCT Filed: Oct. 26, 2007

(86) PCT No.: PCT/EP2007/009318
§ 371 (c)(1),
(2), (4) Date: Mar. 1, 2010

(87) PCT Pub. No.: WO2008/049631
PCT Pub. Date: May 2, 2008

(65) Prior Publication Data
US 2010/0209384 A1    Aug. 19, 2010

(30) Foreign Application Priority Data
Oct. 27, 2006   (EP) .................... 06291679

(51) Int. Cl.
*A61F 13/00*   (2006.01)
*A61K 38/09*   (2006.01)
(Continued)

(52) U.S. Cl.
CPC ............ *A61K 38/30* (2013.01); *A61K 9/0024* (2013.01); *A61K 38/09* (2013.01); *A61K 38/25* (2013.01);
(Continued)

(58) Field of Classification Search
CPC ........ A61K 47/34; A61K 38/30; A61K 38/25; A61K 38/26; A61K 38/27; A61K 38/09; A61F 9/0017
See application file for complete search history.

(56) References Cited

U.S. PATENT DOCUMENTS 5,665,394 A      9/1997   Igari et al.
5,686,110 A  *  11/1997   Greenwald et al. .......... 424/486
(Continued)

FOREIGN PATENT DOCUMENTS

EP    1489126 A    12/2004
GB    2354438 A     3/2001
(Continued)

OTHER PUBLICATIONS

Carbowax and carbowax sentry. Dow chemical corporation. Mar. 2006, 60 pages.*
(Continued)

*Primary Examiner* — Lakshmi Channavajjala
(74) *Attorney, Agent, or Firm* — Hunton & Williams LLP (57) ABSTRACT

The present invention relates to a parenteral, sustained and controlled release, semisolid formulation comprising an end-capped oligomer and at least one active substance without any supplementary viscosity reducing agent or excipient.

32 Claims, 5 Drawing Sheets

(51) Int. Cl.
*A61K 38/30* (2006.01)
*A61K 9/00* (2006.01)
*A61K 38/25* (2006.01)
*A61K 38/26* (2006.01)
*A61K 38/27* (2006.01)
*A61K 47/34* (2017.01)
*A61K 47/36* (2006.01)

(52) U.S. Cl.
CPC .............. *A61K 38/26* (2013.01); *A61K 38/27* (2013.01); *A61K 47/34* (2013.01); *A61K 47/36* (2013.01)

(56) References Cited

U.S. PATENT DOCUMENTS

| | | | |
|---|---|---|---|
| 6,211,249 B1* | 4/2001 | Cohn et al. | 514/772.1 |
| 8,475,829 B2* | 7/2013 | Sebree et al. | 424/426 |
| 2004/0001889 A1* | 1/2004 | Chen et al. | 424/468 |
| 2006/0034923 A1 | 2/2006 | Li et al. | |
| 2006/0147412 A1 | 7/2006 | Hossainy et al. | |

FOREIGN PATENT DOCUMENTS

| | | |
|---|---|---|
| WO | WO 02/090417 | 11/2002 |
| WO | WO 2004/062649 | 7/2004 |
| WO | WO 2005/120453 | 10/2005 |

OTHER PUBLICATIONS

Registry database from CAS (Nov. 16, 1984) 6-D-tryptophan Leutinizing hormone releasing factor (swine).

* cited by examiner

SUSTAINED RELEASE FORMULATIONS COMPRISING VERY LOW MOLECULAR WEIGHT POLYMERS

The present invention relates to a parenteral sustained and controlled release semi-solid formulation comprising an oligomer end-capped and an active substance without any supplementary viscosity reducing agent or excipient.

The present invention further provides continuous release of the active substance over a period of at least one week when the semi-solid is placed in an aqueous physiological environment.

More specifically the invention relates to a pharmaceutical composition in the form of a semi-solid comprising at least one biodegradable very low molecular weight polymer end-capped and at least one active substance. This pharmaceutical composition will be used by parenteral way such as subcutaneous or intramuscular injection and will form an implant/depot composition when administered in an aqueous physiological environment.

The value of administrating active substance in a form of sustained release compositions has been known for a long time.

Various approaches to control the releasing rate of an active substance have been discussed.

Among such strategies, two different approaches have been found to develop implants or microparticles formulations comprising biodegradable polymers such as a poly (lactide-co-glycolide) in which the active substance is incorporated.

A further approach was to develop injectable depot compositions comprising biodegradable polymers and solvents/plasticizers that are very or relatively soluble in aqueous body fluid. In some cases, the diffusion of solvents/plasticizers promote a rapid solidification of the polymer at the implantation site and thus induces a slow releasing of the drug.

In European patent EP 1126822 it has been shown that by combining a thermoplastic polymer or copolymer, an organic solvent, an active substance and a polymeric controlled release additive such as a poly(lactide-co-glycolide)/polyethylene glycol (PLGA/PEG) block copolymer, the releasing rate of the active substance could be controlled. When brought in contact with an aqueous environment, such as body or tissue fluids the organic solvent is supposed to dissipate or disperse into body fluids and concurrently the substantially insoluble thermoplastic base polymer precipitates to form the solid matrix or implant.

Even though depot composition as described in the international patent application WO 2004/012703 can be injected into a desired location within a patient's body to form an implant. Such injectable depot compositions require the use of organic solvents such as benzyl alcohol or benzyl benzoate and a thixotropic agent like ethanol in addition to the drug and polymer. Nevertheless, these additives incorporated into depot composition, thereby may result in low biocompatibility of the product or less stability of active agent incorporated in it.

Furthermore, it is undesirable to find organic solvent residues, generally used during the manufacture of the polymer or implied in the operating mode of the implant itself.

Nevertheless, without addition of viscosity reducing agent such as an organic solvent, either the composition is not fluid enough to be injectable or the injection is made difficult and requires syringe devices with very broad needle and are thus very painful.

Another approach might be achieved by pharmaceutical compositions which are administered by injection and automatically form sustained release gel formulations. Such formulations have been reported in the international patent application WO 96/07398. As disclosed in the text, these compounds were formulated as parenteral sustained release gel formulations without any addition of biodegradable polymers or other carrier matrix to control the peptide release profile.

Figure 3:
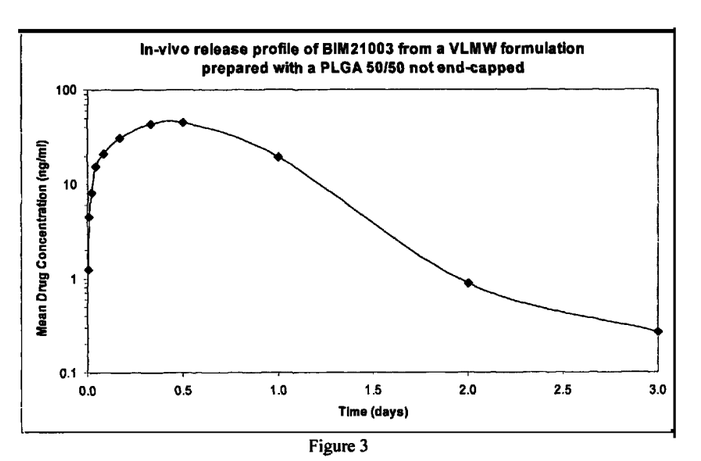
FIG. 3: shows in-vivo release profile of triptorelin (BIM21003) from a VLMW formulation prepared with PLGA 50/50 not end-capped as obtained in example 12.

Within the framework of using VLMW (very low molecular weight) polymers, a previous assay using PLGA with a ratio of 50/50 (i.e., a copolymer of lactic acid and glycolic acid comprising 50% units of lactic acid and 50% of glycolic acid) and having a molecular weight of about 2,300 Daltons, ended by a carboxylic acid group did not disclosed the expected results. A rapid degradation of the polymer was observed when administered in an aqueous physiological environment as illustrated in FIG. 3 and example 12. In addition, one of the major difficulties encountered with such formulations consists in a problem of viscosity and thus requires heating components at about 50-60° C. during manufacturing process and also before injection.

Surprisingly, it has been found that semi-solid implants prepared according to different methods and made of modified very low molecular weight polymer, i.e., a polylactide or copolymer such as PLA, PLGA or mixture thereof and with a capping moiety at the carboxylic extremity, can form subcutaneous/intramuscular depot implants without any supplementary additive before and after injection when placed in an aqueous physiological environment. It was observed that the active substance is released over a period of at least one week and even over one month when administered in an aqueous physiological environment. Furthermore, the unexpected fluidity of such polymers/formulations in their dry form allow the use of conventional devices such as syringe type for parenteral administration. Another valuable advantage of the present invention is to provide compositions which may be used as prefilled (pre-filled syringe for instance) or ready to use formulations.

The end-capping of polymeric chains increases their fluidity, thus facilitating the manufacture of semi-solid formulations and enabling their injection with a conventional device such as syringe type. Administration devices could be 0.3-1 ml plastic syringes with needles having a gauge 16 G and thinner needles. higher needles of 19 G or higher.

The object of the present invention is to specifically provide semi-solid pharmaceutical compositions used as sustained release formulations which release the active substance over of at least one week and even more than one month when the semi-solid formulation is administered in an aqueous physiological environment.

The present invention can be also considered as a specific suspension stable of solid active substance (powder) in a continuous very low molecular weight matrix.

The object of the present invention has been achieved by means of in-vivo and in-vitro tests and with a process as claimed in the present invention.

Unless otherwise indicated the following definitions are set forth to illustrate and define the meaning and scope of the various terms used to describe the invention herein.

The term "very low molecular weight" and "modified very low molecular weight" refers to an end-capped polymer or copolymer, with a weight average molecular weight between 500 and 5,000 Daltons, preferably between 700 and 3,000 Daltons, and more preferably between 800 and 2,000 Daltons.

The term end-capped or capping moiety refers to the grafting of a non-reactive chemical group at the end of a polymeric chain, thus giving to the polymers a better stability against degradation agents.

The term "alkyl" alone or in combination with other groups as used herein refers to a saturated hydrocarbon group including linear, branched, cyclic, unsubstituted, substituted alkyl.

The term "heteroalkyl" refers to an alkyl in which at least one carbon is replaced with a heteroatom.

The term "alkoxy" refers to an alkyl group linked to an oxygen.

The term "aryl" refers to an aromatic substituent containing a single aromatic ring or multiple aromatic rings that are fused together, linked covalently, or linked to a common group such as ethylene or methylene moiety.

The term "substituted aryl" refers to an aryl moiety substituted with one or more substituents groups.

The term heteroaryl refers to an aryl group in which at least one carbon is replaced with a heteroatom.

The term aralkyl refers to an alkyl group substituted with an aryl group.

The term heteroaralkyl refers to an alkyl group substituted with a heteroaryl group.

Preferred end-groups are alkyls groups including linear, branched, cyclic, unsubstituted and substituted derivatives.

By binary semi-solid pharmaceutical composition it is understood a biodegradable pharmaceutically acceptable polymer or a mixture thereof in addition of at least one active substance or a mixture thereof preferably in their dried form.

The useful biodegradable and pharmaceutically acceptable polymers are generally oligomeric hydrocarboxylic acid derivatives. In particular lactic acid and/or glycolic acid, lactide-glycolide derivatives or mixture thereof.

The term pharmaceutically acceptable means in this context physiologically well-tolerated by a mammal or a human.

The term "molecular weight distribution (MW)" including "the weight average molecular weight ($\overline{MW}$)" and "the polydispersity (Ip)" of the polymer refers to measures carried out by any standard method known by the man skilled on the art, for instance by size exclusion chromatography (SEC), also called gel-permeation chromatography (GPC).

Accordingly, the present invention refers to a sustained and controlled release semi-solid formulation/depot implant comprising:

A sustained and controlled release semi-solid formulation comprising:
  a) An end-capped modified very low molecular weight biodegradable end-capped polymer or copolymer or a mixture thereof, having a weight average-molecular weight from 500 to 5,000 Daltons,
  b) At least one active substance or a mixture thereof, wherein the said preparation is carried out without adjunction of additional diluents, plasticizers, solvents or excipients.

The composition further may comprise suitable biodegradable and pharmaceutically acceptable low molecular weight polymers which can be used in formulations disclosed in the present invention and are selected from list but not limited to: polylactides, polyglycolides, poly(lactide-co-glycolide)s, poly(lactic acid)s, poly(glycolic acid)s, polycaprolactones, polyanhydrides, polyamines, polyamides, polyesteramides, polyethers, polyetheresters, polyorthoesters, polydioxanones, polyacetals, polyketals, polycarbonates, polyiminocarbonates, polyphosphoesters, polyorthocarbonates, polyphosphazenes, poly(alkylene alkylate)s, polyurethanes, succinates, poly(malic acid)s, poly(amino acid)s, polyvinylpyrrolidone, polyethylene glycol, polyhydroxycellulose, polysaccharides, poly(propylene fumarate)s, and copolymers, terpolymers and mixtures thereof.

The preferred form of the composition comprises a suitable biodegradable and pharmaceutically acceptable low molecular weight polymer such as polylactides, polyglycolides, poly(lactide-co-glycolide)s, poly(lactic acid)s, poly (glycolic acid)s or a mixture thereof.

Suitable active substances which can be added in formulations disclosed in the present invention are selected from list but not limited to: proteins, enzymes, hormones, polynucleotides, nucleoproteins, polysaccharides, glycoproteins, lipoproteins, peptides, polypeptides, steroids, analgesics, local anesthetics, antibiotic agents, chemotherapeutic agents, immunosuppressive agents, anti-inflammatory agents, antiproliferative agents, antimitotic agents, angiogenic agents, antipsychotic agents, central nervous system (CNS) agents, anticoagulants, fibrinolytic agents, growth factors, antibodies, antigens, ocular drugs, human growth hormone, methionine-human growth hormone, des-phenyl-alanine human growth hormone, glugacon, calcitonin, insulin, heparin, interleukin-1, interleukin-2, Factor Viol, Factor IX, luteinizing hormone, relaxin, ghrelin, follicle-stimulating hormone, atrial natriuretic factor, filgrastim epidermal growth factors (EGFs), platelet-derived growth factor (PDGFs), insulin-like growth factors (IGFs), fibroblast-growth factors (FGFs), transforming-growth factors (TGFs), interleukins (ILs), colony-stimulating factors (CSFs, MCFs, GCSFs, GMCSFs), interferons (IFNs), endothelial growth factors (VEGF, EGFs), erythropoietins (EPOs), angiopoietins (ANGs), placenta-derived growth factors (PlGFs), toxines such as botulinum toxine, and hypoxia induced transcriptional regulators (HIFs) and pharmaceutically acceptable salts of these compounds, or their analogs, fragments or derivatives.

Preferably the active substance of the composition can be a peptide, a polypeptide, a protein such as luteinizing hormone (LHRH) or LHRH analogs, thyroid stimulating hormone (TSH), follicule-stimulating hormone (FSH), parathyroid hormone (PTH), insulin, somatostatin analogs and derivatives, growth hormone, growth hormone releasing hormone (GHRH), growth hormone releasing peptide, calcitonin and pharmaceutically acceptable salts of these compounds, their analogs, fragments or derivatives.

According to the invention the more preferred active substances of the composition is a peptide, a peptide derivative, a polypeptide or a protein such as recombinant human Growth Hormone (rhGH), growth hormone releasing hormone (GHRH), insulin-like growth factors (IGFs) such as IGF-1, GLP-1 analog, luteinizing hormone (LHRH) or LHRH analogs and somatostatin analogs.

Pharmaceutical salts of active substances usable for compositions according to the invention are produced by acid addition salts with organic and inorganic acids. Examples of acid addition salts of compounds are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkyl- and arylsulphonic acids such as methanesulphonic acid, p-toluenesulphonic acid, benzenesulphonic acid and the like, as well as salts with organic carboxylic acids, for example with acetic acid, tartaric acid, maleic acid, citric acid, benzoic acid, fumaric acid, oxalic acid, stearic acid, salicylic acid, ascorbic acid or insoluble salts such as pamoïc acid and the like.

Whether the active substance contains a carboxyl group also form pharmaceutically acceptable salts with bases. Examples of such salts are alkali metal salts, for example sodium and potassium salts, ammonium salts, salts with organic bases, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine, or with amino acids such as arginine and lysine.

Preferred peptide salt is a salt formed with an organic acid.

In a preferred form, the invention relates to modified very low molecular weight polymers or copolymers which comprise units of lactic acid and/or glycolic acid having a molecular weight from 500 to 5,000 Daltons.

Preferred molecular weight of very low molecular weight polymers are from 700 to 3,000 Daltons, especially preferred are between 800 to 2,000.

According to the invention, the polymer may have a monomer ratio of lactic acid/glycolic acid or lactide/glycolide from 100/0 to 50/50, preferably from 100/0 to 80/20.

Preferably the very low molecular weight polymers disclosed in the present invention are end-capped in order to better their stability against degradation agents, and also to increase their physical fluidity thus facilitating manufacturing and injecting processes. Examples of suitable endgroups are alkyl, substituted alkyl, heteroalkyl, alkoxy, aryl, substituted aryl, heteroaryl, aralkyl, heteroaralkyl or another substituent. Preferred end-groups are alkyls groups including linear, branched, cyclic, unsubstituted and substituted derivatives.

More preferred end-groups are linear alkyl groups.

The invention further encompasses a semi-solid pharmaceutical composition/depot implant comprising at least a biodegradable very low molecular weight polymer endcapped with a C5-C18 alkyl moiety instead of its carboxylic acid extremity and an active substance, the said pharmaceutical composition is suitable for the formation of depot/implant at a temperature between 15 to 50° C. which continuously releases the active substance over of at least one week when the pharmaceutical composition is administered in an aqueous physiological environment.

According to the invention preferred polymer end-groups are alkyl groups, among these, there may in particular be alkyl groups containing from 5 to 18 carbon atoms, and more preferably alkyl groups containing from 5 to 12 carbon atoms.

In addition the preferred temperature for parenteral application of the semi-solid pharmaceutical composition/depot implant as herein described is from 25 to 40° C. According to the invention as herein described the amount of active substance incorporated in the low polymeric weight formulation depends upon the desired release profile in relation with the concentration of the active substance required to produce the biological effect and the length of time the substance should be released.

Furthermore, the invention relates to a process for the preparation of a binary semi-solid pharmaceutical composition/depot implants for parenteral application comprising a very low molecular weight biodegradable polymer mixed with at least one active substance.

The first process according to the invention for the preparation of a semi-solid formulation/depot implant mixture may be carried out as follows:
a) Introduction of the active substance and the polymer in two different syringes and fitting the pistons.
b) Connection of the two filled syringes with a 3 cones stainless connector.
c) Removing air from syringe filled with the active substance under vacuum.
d) Mixing the two components by a kneading process between the two syringes, optionally under controlled temperature between 5° C. and 60° C., preferably at room temperature.

In accordance with the invention the pharmaceutical formulations are suitably prepared:
by mixing an appropriate amount of modified very low molecular weight polymer and one active substance or mixture of active substances including physiological safe salt thereof characterized in that the mixture could be made by means of syringes.
the active substance is optionally chosen as a dried powder but could be also a liquid. The dried powder or powder form is preferred.
subsequently closing the filled syringes by a piston.
thereafter connecting the filled syringes by means of a connector.
removing air from the device by a suitable method known by the man skilled on the art for instance vacuum, sonication or microwave. The process is preferably carried out under vacuum when it is required.
thereafter blending the two components by mixing them through the connector.
optionally fluidising the mixture by heating syringes in a manner known per se.

The invention further relates to a second process for providing the semi-solid formulation/depot implant as herein described.

The second process of the invention suitable for the preparation of a semi-solid formulation/depot implant includes the following steps:
a) Mixing the polymer in a blender.
b) Addition of active substance.
c) Mixing of the components at room temperature, optionally under controlled temperature between 5° C. and 60° C.
d) The last step of the process could be carried out under vacuum in order to remove air bubbles.

In accordance with the invention, the pharmaceutical formulations are suitably prepared:
- initiating the blending of the components by means of a specific device characterized in that the representative apparatus used for blending in the illustrative process includes for instance devices in the form of cylinders, with controlled velocity.
- the active substance is optionally chosen as a dried powder but could be also a liquid. The dried powder or powder form is preferred.
- the mixture of the components of the pharmaceutical formulation could be carried out under controlled temperature, the blending is preferably carried out at room temperature.

The invention further relates to a third process for suitably preparing semi-solid formulation/depot implant as herein described.

The third process suitable for the preparation of a semi-solid formulation/depot implant may be carried out as follows:
a) Dissolving the very low molecular weight polymer in a small volume of methylene chloride.
b) Adding the active substance to the polymer solution.
c) While stirring the solution/suspension of polymer and active substance, adding an appropriate volume of heptane.
d) The last step of the process would be carried out under temperature and vacuum in order to remove solvents from the bulk.

In accordance with the invention, the pharmaceutical formulations are suitably prepared:
- dissolving the modified very low molecular weight polymer in a suitable solvent or keeping the polymer dissolved in the solvent used for synthesis and/or purification.
- adding to the polymer solution an appropriate amount of one active substance or mixture of active substances including physiological safe salt thereof.
- the active substance is optionally chosen as a dried powder but could be also a liquid. The dried powder or powder form is preferred.
- subsequently, adding to the mixture a non-solvent of the very low molecular weight polymer, inducing its precipitation and the partly incorporation of active substance.
- the blending of the components of the pharmaceutical formulation could be carried out under controlled temperature, the blending is preferably carried out at room temperature.
- removing solvents from the bulk directly or after the precipitation by a suitable method known by the man skilled on the art, for instance heating under vacuum.

In addition, the whole preparation processes can be controlled regarding temperature, pressure, heating and cooling periods with equipment common to the skilled practitioner.

The active substance can be included in an amount of 0.001 to 70% (w/w), preferably in an amount of 0.1 to 30% (w/w), more preferably in an amount of 2 to 30% (w/w).

The active substance can be suspended, dispersed or dissolved within the semi-solid formulation.

In a further embodiment of the invention, the active substance can be previously treated by lyophilisation, drying, grinding, granulation, extrusion, microencapsulation, complexation or any other suitable method known by the man skilled on the art, before the preparation of the composition.

In addition, any excipient which is not used to reduce the viscosity or improve the injectability of composition, and which is not acting on the polymer, can be optionally used. For instance, every classical excipients used in injectable compositions like stabilizers and surfactants can be added.

Any technique known by the man skilled on the art such as radiosterilisation, autoclave sterilisation or sterile filtration can be used for semi-solid formulation/depot implants as disclosed in the invention to obtain a sterile preparation.

Also encompassed in the invention the preparation of the semi-solid formulation may be realised under aseptic conditions.

The preparation of the semi-solid formulation may be realised extemporaneously i.e. before injection by a kneading process between two pre-filled syringes.

As further embodiment, the semi-solid formulation of the present invention may be conditioned in pre-filled syringes as ready-to-use.

As particular embodiment of the present invention, the semi-solid formulation can be for the treatment and/or prevention of chronic disorders or diseases.

In a particular embodiment of the invention, the sustained and controlled release formulation is injectable.

The following examples serve as illustration of the invention without limiting it.

EXAMPLE 1

Determination of Polymers Weight Average Molecular Weight by Gel Permeation Chromatography Measurements were performed by means of Gel Permeation Chromatography with a Styragel HR1 column (Waters) at 40° C., with tetrahydrofuran (HPLC grade) as eluent at a flow of 0.2 ml/min. Various polystyrene standards having a range of molecular weight between 382 and 4,920 g/mol (Polymer Laboratories) were used for the calibration. The polymers solutions were prepared at 0.4 mg/ml in tetrahydrofuran. The analyses were carried out with a Waters Alliance 2695 chromatographic system equipped with an Evaporative Light Scattering detector (PL-ELS 1000, Polymer Laboratories).

Results are gathered in table 1.

TABLE 1

| Polymer Batch | Composition | Alkyl end-group | Average Mw (Da) | Ip | $Tg^{Onset}$ (° C.) |
|---|---|---|---|---|---|
| J001/3000013 | PLGA 50/50 | no | 2,300 | 1.5 | −3 |
| FB330 | PLA | no | 1,220 | 1.2 | nd |
| FB341 | PLA | C5 | 1,160 | 1.2 | −19 |

TABLE 1-continued

| Polymer Batch | Composition | Alkyl end-group | Average Mw (Da) | Ip | Tg$^{Onset}$ (° C.) |
|---|---|---|---|---|---|
| FB342 | PLGA 80/20 | C5 | 1,250 | 1.2 | −18 |
| MG02.013 | PLA | C5 | 1,220 | 1.1 | −17 |
| MG02.024 | PLA | C5 | 740 | 1.2 | −35 |
| MG02.038 | PLA | C5 | 860 | 1.2 | −32 |
| MG02.073 | PLA | C12 | 960 | 1.2 | −50 |
| MG03.035 | PLA | C5 | 1,120 | 1.1 | −19 |
| MG03.047 | PLA | C5 | 1,010 | 1.1 | −19 |
| MG03.107 | PLA | C12 | 1,400 | 1.2 | −21 |
| MG03.108 | PLA | C18 | 1,430 | 1.1 | −10 |
| MG04.110 | PLA | C5 | 934 | 1.1 | −29 |
| MG05.055 | PLA | C12 | 1,350 | 1.1 | −32 |

EXAMPLE 2

Determination of Polymers Glass Transition Temperature by Differential Scanning Calorimetry Glass transition temperatures were measured using a Differential Scanning Calorimeter (DSC7, Perkin Elmer Instruments) equipped with a Thermal Analysis Controller (TACT/DX, Perkin Elmer Instruments) and a Cooling Accessory (Intracooler 2, Perkin Elmer Instruments). The instrument temperature and enthalpy were calibrated with indium and n-octane used as standards. 5-10 mg of polymer were introduced in an aluminium pan and thereafter sealed with a pierced-cover. An empty pan was used as reference in all cases, and nitrogen was used as the purge gas.

Samples were subjected to a cooling-heating program from ambient temperature to −70° C., held for 10 min at −70° C., and thereafter heated to 20° C. at a rate of 5° C./min. Cooling-heating program was repeated. The glass transition temperature was taken to be the onset of the transition measured from first and second heating steps.

Results are gathered in table 1.

EXAMPLE 3

Preparation of a BIM23190C/VLMW Formulation (Batch N174055)

0.6 g of the somatostatin analog BIM23190C (acetate salt) were introduced in a syringe and 6 g of semi-solid PLA (FB341 batch, see table 1) were introduced in a second syringe. The two syringes were connected with a 3 cones stainless connector. Air was removed from active substance applying vacuum in the first syringe. Mixing BIM23190C with the polymer excipient was achieved by a push-pull kneading process between the two syringes. The system was warmed until 50-60° C. in order to facilitate mixing process.

The mixture (bulk product) was collected in one syringe, therefore divided in 0.3 ml single-dose syringes coupled with 19×0.8 mm needles, and packed in individual aluminium sealed bags. Sterilization of packed product was performed by gamma-irradiation at 25 kGy in dry ice. The finished product was stored at −22° C.

The content and purity of active substance were controlled by reverse-phase liquid chromatography. The formulations were co-dissolved in acetonitrile and a solution of acetic acid 0.1% (20/80 v/v). Measurements were performed with a Symmetry $C_{18}$, column (Waters) at 40° C., using an elution gradient with an acetonitrile/trifluoroacetic acid solution (0.1%). The analyses were carried out with HPLC pumps (Waters 515) equipped with a Waters pump control module, a Waters 717Plus Autosampler, a Spark Mistral oven and a Waters 486 Tunable Absorbance Detector at 280 nm.

The content of BIM23190 in the finished product was determined to be about 7.7% (w/w) and the area of BIM23190 peak represented 97.1% of the total area.

Results are gathered in table 2.

TABLE 2

| Formulation Batch | Polymer Batch | Active substance | Content (%) | Purity (%) | SIF$^{max}$ (N) |
|---|---|---|---|---|---|
| N174055 | FB341 | BIM23190 | 7.7 | 97.1 | nd |
| N174088 | FB341 | BIM51077 | 10.2 | 95.7 | 24 |
| N182045 | FB342 | BIM21003 | 9.1 | 98.8 | 24 |
| N182054 | MG02.013 | BIM51077 | 8.9 | 95.1 | 21 |
| N193075 | MG03.035 | BIM21003 | 10.7 | 98.7 | 35 |
| D009099 | MG04.110 | BIM21003 | 2.0 | 98.7 | 3 |

EXAMPLE 4

Preparation of a BIM51077C/VLMW Formulation (Batch N182054)

7.0 g of semi-solid PLA (MG02.013 batch, see table 1) were placed between the two cylinders of a blender (AR400, Erweka). While the polymer was slowly mixed with the system, 0.70 mg of GLP-1 analog BIM51077C (acetate salt) were slowly introduced through a funnel. An homogeneous composition was achieved at room temperature after 2 hours of slow mixing with this system. After collecting the mixture (bulk product) in a 10 ml plastic syringe, the bulk was placed under vacuum at room temperature for 30 minutes in order to remove air bubbles introduced during the mixing process.

Bulk product was therefore divided in 0.3 ml single-dose syringes coupled with 19×1.2 mm needles, and packed in individual aluminium sealed bags. The sterilization of the packed product was performed by gamma-irradiation at 25 kGy in dry ice. The finished product was stored at −22° C.

The content and purity of the active substance were controlled by reverse-phase liquid chromatography. The formulations were co-dissolved in acetonitrile and a solution of acetic acid 0.1 M (20/80 v/v). The measurements were performed with a Symmetry 618 column (Waters) at 50° C., using an elution gradient with triethylamine phosphate buffer (pH 2.3)/acetonitrile. Analyses were carried out with a Waters Alliance 2695 chromatographic system equipped with a Waters 2487 Dual λ Absorbance Detector at 220 nm.

The content of BIM51077 in the finished product was determined to be about 8.9% (w/w) and the peak area of BIM51077 represented 95.1° A) of the total area.

Another 10% BIM51077 semi-solid formulation (N174088 batch) was also prepared as above described with a VLMW PLA (FB341 batch).

Results are gathered in table 2.

EXAMPLE 5

Preparation of a BIM210036/VLMW Formulation (Batch N182045)

3.8 g of semi-solid PLGA 80/20 (FB342 batch, see table 1) were placed between the two cylinders of a blender (AR400, Erweka). While the polymer was slowly mixed with the system, 0.42 mg of triptorelin BIM21003C (acetate salt) were slowly introduced through a funnel. An homogeneous composition was achieved at room temperature after 2 hours of slow mixing with this system. The mixture (bulk product) was collected in a 10 ml plastic syringe, thereafter divided in 0.3 ml single-dose syringes coupled with 19×1.2 mm needles, and packed in individual aluminium sealed bags. Sterilization of packed product was performed by gamma-irradiation at 25 kGy in dry ice. Finished product was stored at −22° C.

The content and purity of the active substance were controlled by reverse-phase liquid chromatography. The formulations were co-dissolved in acetonitrile and a solution of acetic acid 0.1% (20/80 v/v). The measurements were performed with a Symmetry $C_{18}$ column (Waters) at 40° C., using an elution gradient with acetonitrile/trifluoroacetic acid solution (0.1%). Analyses were carried out with HPLC pumps (Waters 515) equipped with a Waters pump control module, a Waters 717Plus Autosampler, a Spark Mistral oven and a Waters 486 Tunable Absorbance Detector at 280 nm.

The content of BIM21003 in the finished product was determined to be about 9.1% (w/w) and the peak area of BIM21003 represented 98.8% of the total area.

Results are gathered in table 2.

EXAMPLE 6

Preparation of a BIM21003C/VLMW Formulation (Batch N193075)

0.55 g of triptorelin BIM21003C (acetate salt) were introduced in a syringe and 5.0 g of semi-solid PLA (MG03.035 batch, see table 1) were introduced in a second syringe. After connecting the syringes, mixing BIM21003C with polymer excipient was achieved by a push-pull kneading process between the two syringes at about 55° C.

The mixture (bulk product) was collected in one syringe, therefore divided in 0.3 ml single-dose syringes coupled with 19×1.2 mm needles, and packed in individual aluminium sealed bags. Sterilization of packed product was performed by gamma-irradiation at 25 kGy in dry ice. Finished product was stored at −22° C.

Content and purity of active substance were controlled by reverse-phase liquid chromatography as described in example 5.

The content of BIM21003 in the finished product was determined to be about 10.7% (w/w) and the area of BIM21003 peak represented 98.7% of the total area.

Results are gathered in table 2.

EXAMPLE 7

Preparation of a BIM21003C/VLMW Formulation 0.19 g of triptorelin BIM21003C (acetate salt) were introduced in a syringe and 7.8 g of semi-solid PLA (MG04.110 batch, see table 1) were introduced in a second syringe. After connecting the syringes, mixing BIM21003C with polymer excipient was achieved by a push-pull kneading process between the two syringes at room temperature.

The mixture (bulk product) was collected in one syringe, therefore divided in 0.3 ml single-dose syringes coupled with 19×1.2 mm needles, and packed in individual aluminium sealed bags. Sterilization of packed product was performed by gamma-irradiation at 25 kGy in dry ice. Finished product was stored at −22° C.

Content and purity of active substance were controlled by reverse-phase liquid chromatography as described in example 5.

The content of BIM21003 in the finished product was determined to be about 2.0% (w/w) and the area of BIM21003 peak represented 98.7° A) of the total area.

Results are gathered in table 2.

EXAMPLE 8

Evaluation of the Injectability by Indirect Estimation of the Viscosity

The relative injectable viscosity of the formulations was determined by means of a Dinamometer (L1000R, Lloyd Instruments) equipped with a cell force (NLC 100 N, Lloyd Instruments). The finished compositions packed in 0.3 ml single-dose syringes coupled with 19×1.2 mm needles were held 2 hours at room temperature before the measurements.

Pre-filled syringes were subjected to a piston compression at 100 mm/min while the injection force has been recorded. The maximum value of the force was reported as the Maximum Syringe Injection Force ($SIF^{max}$) in Newtons.

Results are gathered in table 2.

EXAMPLE 9

In-Vitro Release Assay with a BIM51077C/VLMW Formulation (Batch N174088)

An in-vitro assay was performed with a semi-solid formulation of 10% BIM51077 using a PLA ended with $C_5$ alkyl-group. The preparation of this composition, its conditioning, sterilization and analytical control are described in example 4.

An in-vitro static release assay was performed with a dialysis device in a phosphate buffer solution pH 7.4 (European Pharmacopoeia) at 37° C. Around 140 mg of finished product were introduced in a dialysis cylindrical membrane (Ø3.5 mm, M.W.C.O 25 kD, Spectra Por) thereafter the dialysis device was placed in 20 ml of the phosphate buffer at 37° C. The incubation media were collected for analysis during the assay and replaced by 20 ml of buffer at 37° C. The incubation media were therefore analyzed by RP-HPLC (as described in example 4) in order to determine the amount of active substance released. Each experiment was done independently in triplicate.

Figure 1:
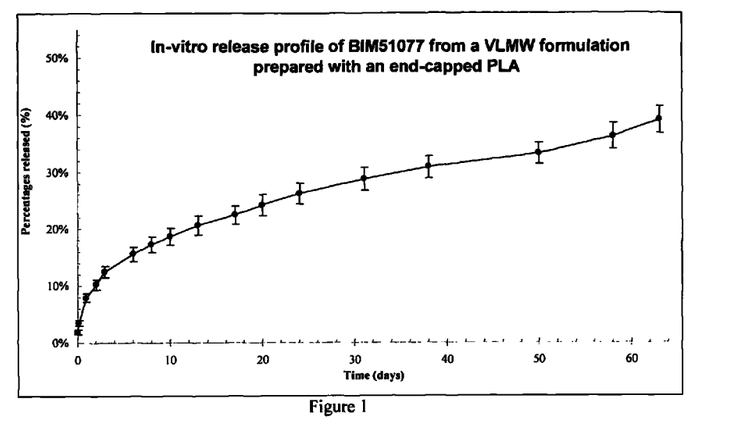
FIG. 1: shows in-vitro release profile of GLP-1 analog (BIM51077) from a VLMW formulation prepared with an end-capped PLA as obtained in example 9.

BIM51077 in-vitro release profile is shown in FIG. 1.

EXAMPLE 10

In-Vitro Release Assay with a BIM21003C/VLMW Formulation (Batch N182045)

An in-vitro assay was performed with a semi-solid formulation of 9% BIM21003 using a PLGA 80/20 ended with $C_5$ alkyl-group. The preparation of this composition, its conditioning, sterilization and analytical control are described in example 5.

In-vitro static release assay was performed with a dialysis device in a Phosphate Buffer Solution pH 7.4 (European Pharmacopoeia) at 37° C. Around 130 mg of finished product were introduced in a dialysis cylindrical membrane (Ø3.5 mm, M.W.C.O 25 kD, Spectra Por) and dialysis device was placed in 20 ml of buffer at 37° C. Incubation media were collected for analysis during the assay and replaced by 20 ml of buffer at 37° C. Incubation media were therefore analyzed by spectrophotometry UV-Visible at 280 nm in order to determine the amount of active substance released. Each experiment was done independently in triplicate.

Figure 2:
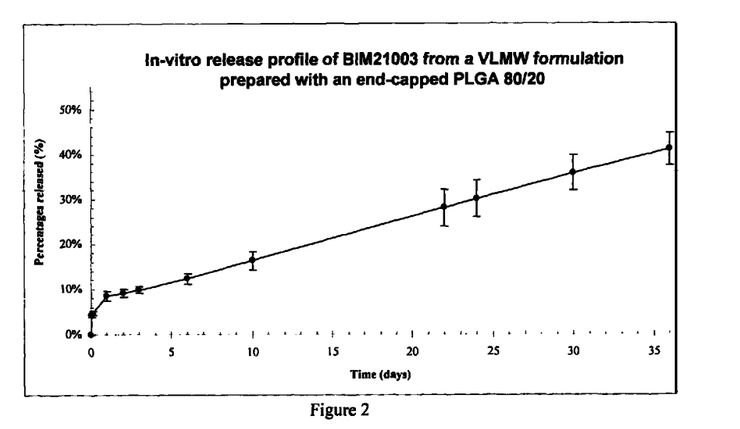
FIG. 2: shows in-vitro release profile of triptorelin (BIM21003) from a VLMW formulation prepared with an end-capped PLGA 80/20 as obtained in example 10.

BIM21003 in-vitro release profile is shown in FIG. 2.

EXAMPLE 11

BIM21003C/VLMW Formulation Prepared by Precipitation

The VLMW polymer used in this composition was a modified PLA with a C5 alkyl end-group and a weight average molecular weight Mw of about 1,140 Daltons. Around 180 mg of triptorelin BIM21003C (acetate salt) were added to 1.0 g of VLMW polymer dissolved in 0.5 ml of methylene chloride. While a suspension of BIM21003C was stirred, 7.5 ml of heptane were added to precipitate the polymer. Thereafter the suspension was filtered and the precipitated mixture was dried under vacuum at 50° C.

The content and purity of the active substance were controlled by reverse-phase liquid chromatography as described in example 5. The content of BIM21003 in the bulk product was determined to be about 7.2% (w/w) and the peak area of BIM21003 represented 98.7% of the total area.

The in-vitro static release assay was performed in duplicate as described in example 10.

EXAMPLE 12

In-Vivo Release Assay in Beagle Dogs with a VLMW Polymer not End-Capped

An in-vivo assay was performed with a semi-solid formulation of 10% BIM21003 using a PLGA 50/50 ended by a carboxylic acid group (J001/3000013 batch, see table 1). The preparation of the formulation was achieved by a push-pull kneading process with 2 syringes at about 50° C. as described in example 6. The mixture (bulk product) was conditioned in a 0.3 ml single-dose syringes coupled with 20×1.4 mm needles thereafter packed in individual aluminium sealed bags, and sterilized by gamma-irradiation at 25 kGy in dry ice.

The content and purity of active substance were controlled by reverse-phase liquid chromatography as described in example 5. The content of BIM21003 in the finished product was determined to be about 11.2% (w/w) and the peak area of BIM21003 represented 95.9% of the total area.

Six male Beagle dogs were administered intramuscularly with single-dose syringes previously heated at 50° C. for 3 min in order to improve its fluidity and facilitate its injection. Syringes were weighted before and after administration, and the injected dose of BIM21003 was calculated to be about 3.6 mg per animal.

Four-ml blood samples were obtained from cephalic veins at specified time intervals post-administration. The blood samples were placed in tubes containing an anticoagulant (15% EDTA.$K_3$ aqueous solution) and a preservative (Trasylol®). After centrifugation, plasma was removed and samples were stored below −20° C. until RIA analysis. The plasma levels of BIM21003 obtained are shown in FIG. 3.

After 3 days post-administration, BIM-21003 plasma levels were below the limit of quantification. Thus, a relatively rapid absorption of drug was observed. These results might be due to the rapid degradation of the polymer as observed in in-vitro experiments performed at 37° C. in aqueous physiological medium.

EXAMPLE 13

In-Vivo Release Assays in Spraque-Dawley Rats with Several Peptides Formulations Several in-vivo assays were performed with semi-solid formulations containing the following peptides: BIM23190C, BIM51077C or BIM21003C (acetate salts). The preparation of these compositions, their conditioning, sterilization, analytical control and in-vitro assays are described in the previous examples. Their characteristics are gathered in table 2.

Twelve male Sprague-Dawley rats were administered subcutaneously with single-dose syringes. The syringes were weighted before and after administration in order to check the total administration of semi-solid formulation. Blood samples of 1.5 ml were obtained through the retro-orbital sinus by means of Pasteur micro-pipettes, under isoflurane-anaesthetized animals (4 sampling times per rat) at specified time intervals post-administration. Blood samples were placed in tubes containing an anticoagulant (15% EDTA.$K_3$ aqueous solution) and a preservative (Trasylol®). After centrifugation, the plasma was removed and samples were stored below −20° C. until RIA or SPE-HPLC-MS/MS analysis (analysis method depending on the therapeutic agent).

Figure 4:
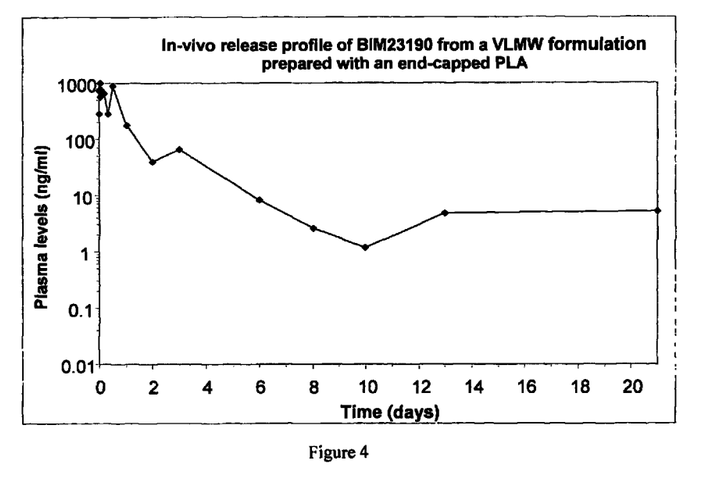
FIG. 4: shows in-vivo release profile of somatostatin analog (BIM23190) from a VLMW formulation prepared with an end-capped PLA as obtained in example 13.

Plasma levels obtained with BIM23190 released from N174055 formulation are shown in FIG. 4. A sustained release until at least 21 days was observed after the administration of a 3.3 mg dose.

Figure 5:
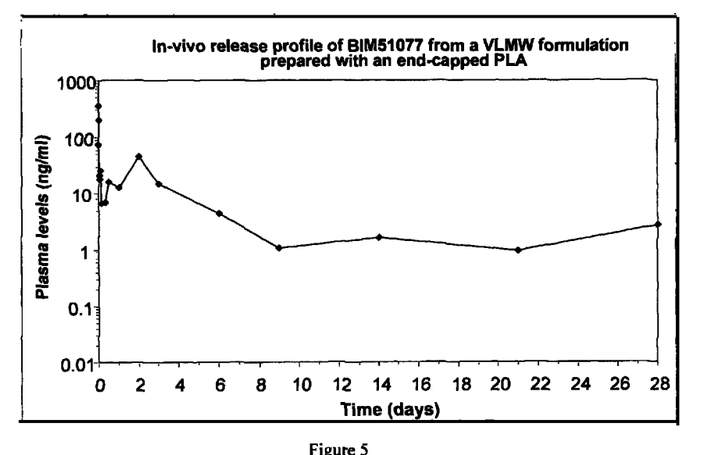
FIG. 5: shows in-vivo release profile of GLP-1 analog (BIM 51077) from a VLMW formulation prepared with an end-capped PLA as obtained in example 13.

Plasma levels obtained with BIM51077 released from N182054 formulation are shown in FIG. 5. A sustained release until at least 28 days was observed in the case of a 4.6 mg of BIM51077 administrated.

Figure 6:
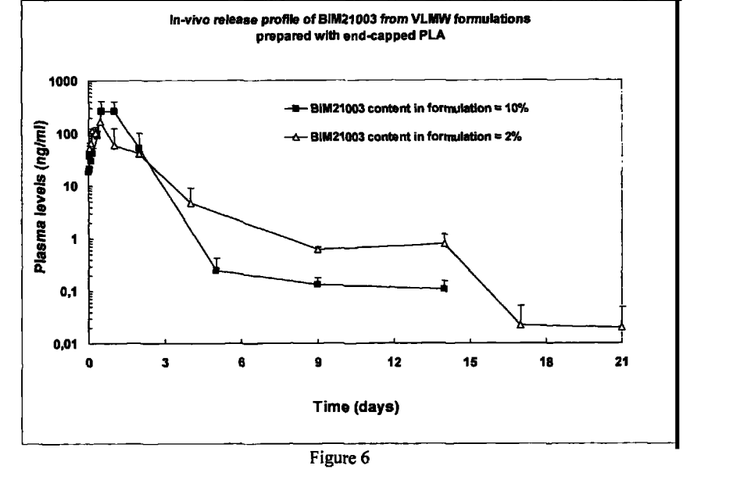
FIG. 6: shows in-vivo release profiles of triptorelin (BIM 21003) from VLMW formulations prepared with end-capped PLA as obtained in example 13.

Plasma levels obtained with BIM21003 released from N193075 and D009099 formulations are shown in FIG. 6. In the case of N193075 formulation, the content of BIM21003 was about 10.7% (w/w) in the formulation and the release of a 3.1 mg dose was observed for 14 days post-administration. In the case of D009099 formulation, the content of BIM21003 was about 2.0% (w/w) in the formulation and the release of a 2.8 mg dose was observed for 21 days post-administration.

EXAMPLE 14

In-Vivo Release Assays in Sprague-Dawley Rats with Growth Hormone Formulations Several semi-solid compositions were prepared with rhGH (recombinant human Growth Hormone). The growth hormone used contained sodium bicarbonate, sucrose and polysorbate 20 in order to stabilize it. Three batches of very low molecular weight PLA were used, with different viscosities: high, medium and low. The polymers characteristics are gathered in table 1.

Semi-solid polymers were previously sterilized by gamma-irradiation at 25 kGy in dry ice. Under aseptic conditions, appropriate amounts of rhGH (freeze-dried) and semi-solid PLA were introduced in two different syringes. After connecting the syringes, an homogeneous mixture was achieved by a push-pull kneading process between the two syringes. The mixture (bulk product) was collected in one syringe, and therefore divided in 0.3 ml single-dose syringes coupled with needles. Finished product was stored at 5° C.

The composition of these formulations, their conditioning and dose administered are gathered in table 3.

TABLE 3

| Formulation Batch | Polymer Batch | Content (%) | Needle | Dose (mg/kg) |
|---|---|---|---|---|
| N203036 | MG03.047 (high viscous) | 12 | 18G | 9 |
| N203052 | MG02.038 (medium viscous) | 15 | 21G | 12 |
| N203075 | MG02.073 (low viscous) | 15 | 21G | 14 |
| N203069 | MG02.038 (medium viscous) | 15 | 21G | 29 (Athymic) 25 (Hypox) |

Six male Sprague-Dawley rats were administered subcutaneously with single-dose syringes. The syringes were weighted before and after administration in order to check the total administration of semi-solid formulation. Blood samples of 0.4 ml were obtained through the retro-orbital sinus by means of Pasteur micro-pipettes, under isoflurane-anaesthetized animals at specified time intervals until 7 days post-administration. Blood samples were placed into tubes and centrifuged. The serum samples were therefore decanted and kept rapidly in a −80° C. freezer until their analysis by means of a ELISA method.

Figure 7:
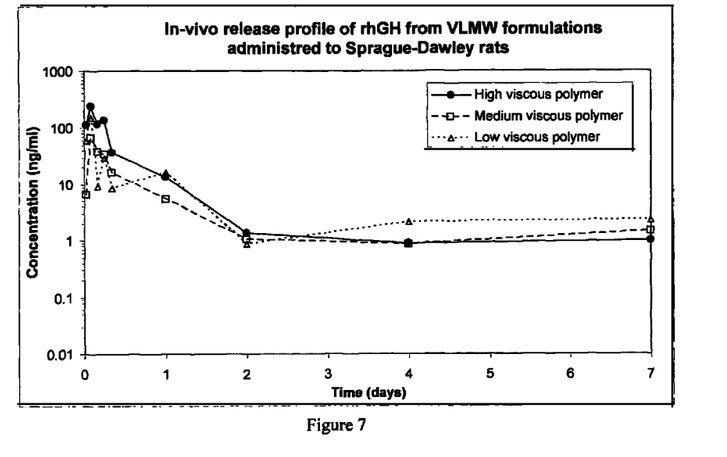
FIG. 7: shows in-vivo release profile of recombinant human Growth Hormone (rhGH) from VLMW formulations administered to Sprague-Dawley rats as obtained in example 14.

Serum concentrations obtained with growth hormone are shown in FIG. 7.

A sustained release until at least 7 days was observed, with rhGH serum concentrations almost constant from 2 to 7 days post-administration.

EXAMPLE 15

In-Vivo Release Assay in Athymic Rats with a Growth Hormone Formulation

In order to assess the release profile of growth hormone after 7 days post-administration of a VLMW formulation, an in-vivo assay was performed with Athymic rats that congenitally lack the thymus gland.

Another growth hormone composition was prepared as described in example 14 (N203069 batch) with a medium viscosity PLA. Its composition, conditioning and the dose administered are gathered in table 3.

Ten female Athymic rats were administered subcutaneously with single-dose syringes. The syringes were weighted before and after administration in order to check the total administration of semi-solid formulation (see table 3).

Figure 8:
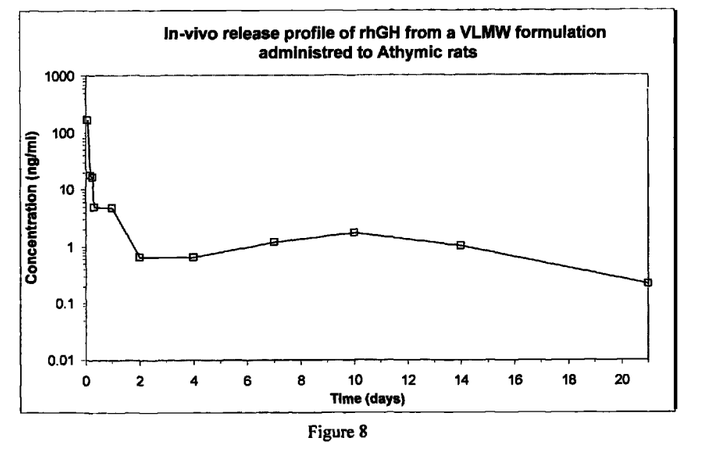
FIG. 8 shows in-vivo release profile of recombinant human Growth Hormone (rhGH) from a VLMW formulation administered to Athymic rats as obtained in example 15.

Serum concentrations obtained with growth hormone are shown in FIG. 8.

A sustained release was observed until 21 days post-administration.

EXAMPLE 16

In-Vivo Release Assay in Hypox Rats with a Growth Hormone Formulation

In order to assess the efficacy of growth hormone released from VLMW formulations, N203069 composition (see table 3 and example 15) was also administered to hypophysectomized (Hypox) Sprague-Dawley rats.

Five female Hypox rats were administered subcutaneously with single-dose syringes. The syringes were weighted before and after administration in order to check the total administration of semisolid formulation (see table 3)

Figure 9:
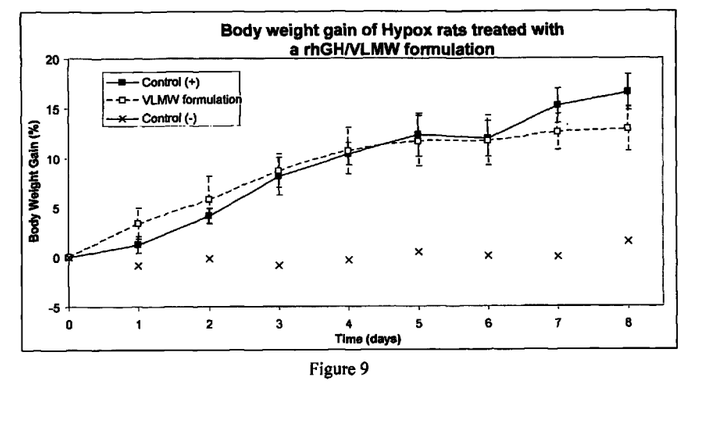
FIG. 9: shows body weight gain of Hypox rats treated with a rhGH/VLMW formulation as obtained in example 16.
Figure 10:
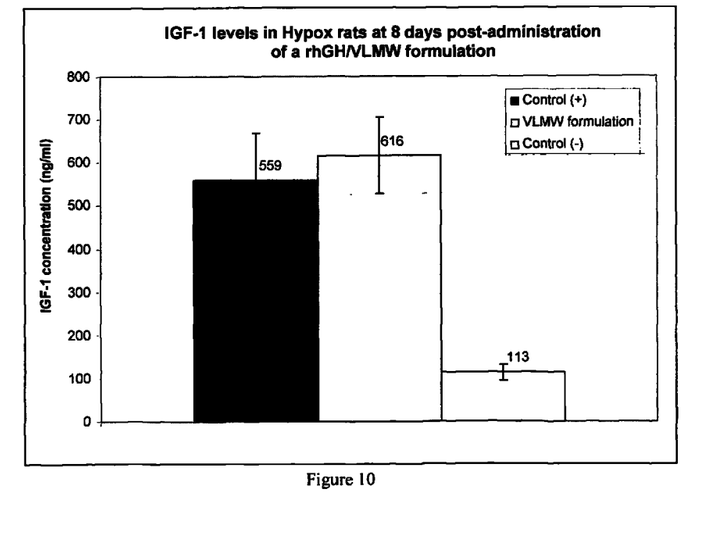
FIG. 10: shows IGF-1 levels in Hypox rats at 8 days post-administration of a rhGH/VLMW formulation as obtained in example 16.

The body weight gains are shown in FIG. 9 and the IGF-1 concentrations are shown in FIG. 10. Results are compared with values obtained after the administration of a placebo "control (−)", and the daily administration of a rhGH aqueous solution of (2 mg/kg/day) "control (+)".

At 8 days post-administration, the body weight profile and IGF-1 level obtained with growth hormone released from VLMW formulation are close to control (+) values.

The invention claimed is:

1. A composition comprising:
   (a) an end-capped, biodegradable polymer or copolymer having a weight average molecular weight of from about 500 to about 5,000 Daltons;
      wherein the polymer or copolymer is a polylactide, polyglycolide, poly(lactide-co-glycolide), poly(lactic acid), or poly(glycolic acid) that is end-capped with an alkyl moiety; and
   (b) a pharmaceutically active substance;
      wherein the pharmaceutically active substance is recombinant human growth hormone (rhGH), growth hormone releasing hormone (GHRH), insulin-like growth factor (IGF), a GLP-1 analog, luteinizing hormone releasing hormone (LHRH), LHRH analog, or somatostatin analog;
   wherein the composition:
      is a sustained and controlled release semi-solid that does not include diluents, plasticizers, solvents or excipients; and
      releases the pharmaceutically active substance over a period of at least one week following administration in an aqueous physiological environment.

2. The composition of claim 1, wherein the alkyl moiety is an alkyl group containing from 5 to 18 carbon atoms.

3. The composition of claim 1, wherein the alkyl moiety is an alkyl group containing from 5 to 12 carbon atoms.

4. The composition of claim 1, wherein the alkyl moiety is an alkyl group containing 5 carbon atoms.

5. The composition of claim 1, wherein the composition forms a sustained release semi-solid formulation/depot implant at an application or injection temperature between about 15° and about 50° C.

6. The composition of claim 5, wherein the composition forms a sustained release semi-solid formulation/depot implant at an application or injection temperature between about 25° and about 40° C.

7. The composition of claim 1, wherein the molecular weight of the polymer or copolymer is between about 700 and 3,000 Daltons.

8. The composition of claim 1, wherein the pharmaceutically active substance is recombinant human growth hormone (rhGH) or growth hormone releasing hormone (GHRH).

9. The composition of claim 1, wherein the pharmaceutically active substance is an insulin-like growth factor (IGF) or a pharmaceutically acceptable salt thereof.

10. The composition of claim 1, wherein the pharmaceutically active substance is a GLP-1 analog or a pharmaceutically acceptable salt thereof.

11. The composition of claim 1, wherein the pharmaceutically active substance is luteinizing hormone releasing hormone (LHRH), a LHRH analog, or a pharmaceutically acceptable salt thereof.

12. The composition of claim 1, wherein the pharmaceutically active substance is a somatostatin analog or a pharmaceutically acceptable salt thereof.

13. The composition of claim 1, wherein about 0.001% to about 70% (w/w) of the composition is a pharmaceutically active substance or a mixture of pharmaceutically active substances.

14. A process for the preparation of the composition of claim 1, comprising:
(a) introducing the active substance or mixture thereof into a first syringe;
(b) introducing the polymer or copolymer into a second syringe;
(c) fitting a piston onto the first syringe;
(d) fitting a piston onto the second syringe;
(e) connecting the first syringe with the second syringe using a cone connector;
(f) removing air from the first syringe; and
(g) mixing the contents of the first and second syringe, wherein the process is carried out without adjunction of diluents, plasticizers, solvents, or excipients.

15. The process of claim 14, wherein one or more steps is carried out at a temperature between about 5° C. and about 60° C.

16. The process of claim 14, further comprising the step of mixing the polymer or copolymer with the active substance or mixture thereof at a temperature between about 5° C. and about 60° C.

17. The process of claim 16, wherein the active substance or mixture thereof is a powder.

18. A composition made by the process of claim 16.

19. The composition of claim 7, wherein the polymer or copolymer has a weight average molecular weight of between about 800 and about 2,000 Daltons.

20. The composition of claim 13, wherein about 0.1% to about 30% (w/w) of the composition is a pharmaceutically active substance or mixture of pharmaceutically active substances.

21. The composition of claim 20, wherein about 2% to about 30% (w/w) of the composition is a pharmaceutically active substance or mixture of pharmaceutically active substances.

22. The process of claim 15, wherein the temperature is room temperature.

23. The process of claim 16, wherein the temperature is room temperature.

24. The process of claim 16, wherein the mixing is performed in a blender.

25. The process of claim 24, wherein the polymer or copolymer is first added to the blender and the active substance or mixture thereof is added while mixing.

26. The composition of claim 1, wherein the insulin-like growth factor is IGF-1.

27. The composition of claim 1, wherein the composition releases the pharmaceutically active substance over a period of at least one month following administration in an aqueous physiological environment.

28. The composition claim 1, wherein the composition releases the pharmaceutically active substance over a period of at least 21 days following administration in an aqueous physiological environment.

29. The composition of claim 1, wherein the alkyl moiety is a linear alkyl.

30. A composition consisting of:
(a) an end-capped, biodegradable polymer or copolymer having a weight average molecular weight of from about 800 to about 2,000 Daltons, or a mixture thereof;
wherein the polymer or copolymer is a polylactide, polyglycolide, poly(lactide-co-glycolide), poly(lactic acid), or poly(glycolic acid), and
wherein the polymer or copolymer is end-capped with an alkyl moiety; and
(b) at least one pharmaceutically active substance;
wherein the composition is a semi-solid.

31. The composition of claim 11, wherein the LHRH analog is triptorelin.

32. The composition of claim 1, wherein the pharmaceutically active substance is growth hormone releasing hormone (GHRH).

* * * * *